United States Patent [19]

Sawyers et al.

[11] Patent Number: 5,018,203
[45] Date of Patent: May 21, 1991

[54] NOISE ATTENUATION

[75] Inventors: Craig G. Sawyers, St. Neots; Gordon M. Edge, Nr. Saffron Walden, both of England

[73] Assignee: Scientific Generics Limited, Cambridge, England

[21] Appl. No.: 399,451

[22] PCT Filed: Feb. 23, 1988

[86] PCT No.: PCT/GB88/00115

§ 371 Date: Oct. 23, 1989

§ 102(e) Date: Oct. 23, 1989

[87] PCT Pub. No.: WO88/06779

PCT Pub. Date: Sep. 7, 1988

[30] Foreign Application Priority Data

Feb. 24, 1987 [GB] United Kingdom ................. 8704314

[51] Int. Cl.$^5$ ............................................ G10K 11/16
[52] U.S. Cl. .......................................... 381/71; 381/96
[58] Field of Search ............................ 381/96, 71, 59

[56] References Cited

U.S. PATENT DOCUMENTS 2,387,845  10/1945  Harry .
2,972,018   2/1961  Hawley et al. .
4,712,247  12/1987  Swarte ................................. 381/96

FOREIGN PATENT DOCUMENTS 313348   2/1915  Fed. Rep. of Germany .
2814093  8/1979  Fed. Rep. of Germany .
1530814 11/1978  United Kingdom .
2132053  6/1984  United Kingdom .
2160070 12/1985  United Kingdom .

OTHER PUBLICATIONS

Patent Abstracts of Japan, vol. 6, No. 173, 09/07/1982.

Primary Examiner—Forester W. Isen
Attorney, Agent, or Firm—Jeffers, Hoffman & Niewyk

[57] ABSTRACT

Apparatus for attenuating noise, particularly in an aircraft cabin, comprising a diaphragm (10) one side of which is subjected to the noise, sensing means (16) for sensing the displacement of the diaphragm in response to the noise, and deflecting means (20) responsive to the sensing means for deflecting the diaphragm in order to cancel the displacement, to attenuate noise transmitted from one side of the diaphragm to the other side of the diaphragm.

24 Claims, 1 Drawing Sheet

NOISE ATTENUATION

Conventional noise attenuation techniques rely either on the generation of anti-sound (i.e. the generation of sound waves in anti-phase to the sound to be attenuated) or on the use of heavy sound absorbing or sound reflecting barriers. These techniques are not suitable for all applications. For example, the attenuation of noise to which airline passengers are subjected is a special problem which the invention aims to solve.

According to one aspect of the invention apparatus for attenuating noise comprises a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm.

The invention therefore relies on the use of a diaphragm which is driven by the deflecting means in order to simulate a structure with a very high stiffness and hence a very high attenuation of transmitted sound.

The diaphragm may be tensioned, e.g. in a surrounding frame, and the deflecting means are preferably driven from the sensing means through a negative feedback loop which acts to null the displacement of the diaphragm, with the result that little or no sound is transmitted from the one side of the diaphragm to the other side of the diaphragm.

The deflecting means may be electrostatic in nature, in which case the diaphragm is preferably a flexible metal or a metallised or otherwise conductively coated plastics film to which a D.C. polarising voltage is applied disposed between two fixed perforated electrodes between which a deflecting voltage is applied. The D.C. polarising voltage may also be supplied by coating the perforated fixed electrodes with an electret material. The deflecting means may alternatively be piezoelectric, in which case the diaphragm may be a polyvinylidene fluoride (PVDF) film with opposed metallised surfaces providing the metal electrodes to which the deflecting voltage is applied. The application of a differential voltage between the electrodes causes the PVDF film to distort so that the film elongates and thins and thereby deflects in the required manner. As an alternative to PVDF film, electro thermomechanical film (ETMF) may be used. This is a material which behaves in a similar fashion to PVDF in that it distorts on application of a deflecting voltage applied across metal electrodes. A further possibility for the deflecting means is to use an electro mechanical arrangement comprising a film printed with a wiring "coil" cooperating with magnets.

The sensing means may be any of the above forms of deflecting means, or may alternatively be optical in character, such as an interferometer, focus probe or optical triangulation. Alternatively, other methods for proximity detection can be employed such as capacitive or inductive techniques.

In order to cope with complex phases of the sound impinging on the diaphragm, the latter may be divided up into separate areas, each area having a corresponding sensing means cooperating with a deflecting means, so that each area of the diaphragm is separately driven and can respond to the variation of sound impinging on that area.

As previously mentioned, the invention was devised specifically for reducing the noise reaching the ears of airline passengers. Ambient noise in aircraft is caused largely by the flow of air past the aircraft fuselage and wings and, to a lesser extent, by the aircraft engines. The requirement is for a lightweight easily fitted noise attenuating means which will be accepted by the travelling public and over which public address messages, film soundtracks or other audio information can be transmitted. For this application the invention is conveniently made in the form of headphones with each earpiece having a tensioned diaphragm which covers the user's ear when worn. Public address messages, film soundtracks and other audio information can be fed to the headphones and superimposed on the deflecting means driving the diaphragm. The diaphragm may be divided into four areas, with each area having a corresponding sensing means for sensing the displacement of that diaphragm area and a deflecting means for driving that diaphragm area to servo the displacement to zero.

Alternatively the diaphragm may be incorporated elsewhere in an aircraft cabin, e.g. in a seat back or in a bulkhead.

According to another aspect of the invention a method of attenuating noise impinging on one side of a diaphragm comprises sensing the actual displacement of the diaphragm in response to the noise and deflecting the diaphragm in order to cancel the displacement, in order to attenuate the noise transmitted from one side of the diaphragm to the other side of the diaphragm.

The invention will now be described by way of example with reference to the accompanying drawings in which.

Figure 1:
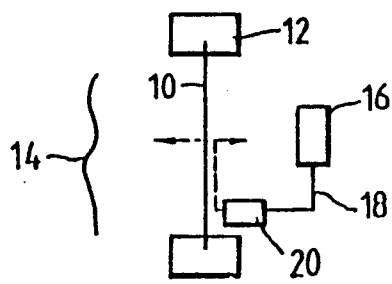
FIG. 1 is a diagrammatic illustration of attenuating apparatus according to the invention.

Referring to FIG. 1, the attenuating apparatus is in the form of a pair of headphones at each earpiece of which there is a thin, lightweight diaphragm 10 held in a tensioned condition in a frame 12. The headphones are intended for use by airline passengers in order to attenuate ambient noise in the aircraft cabin. This noise is indicated diagrammatically by the pressure wave 14 in FIG. 1. The pressure wave 14 impinges on the left hand side of the diaphragm 10, as illustrated in FIG. 1, and this tends to cause the diaphragm 10 to deflect, as indicated by the double headed arrow. Diaphragm deflection is sensed by sensing means 16 which are linked through a feedback connection 18 to deflecting means 20 which act to deflect the diaphragm 10 so as to cancel out the displacement caused by the incident pressure wave 14. The displacement of the diaphragm 10 is therefore constantly servoed to zero with the result that the thin lightweight diaphragm 10 is made to simulate a structure with a very high stiffness and consequently a very high noise attenuation of transmitted sound. Hence, very little of the incident sound is transmitted through the diaphragm 10 to the right hand side thereof where the wearer's eardrum will be located.

Figure 2:
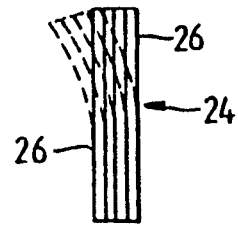
FIGS. 2 through 5 show four alternative forms of diaphragm for use in the apparatus of FIG. 1.

The diaphragm 10 may be formed by multiple layers of polyvinylidene fluoride (PVDF) film, as indicated at 24 in FIG. 2, where the thickness of each layer is exaggerated. The individual layers are bonded together and a deflecting voltage from the deflecting means 20 is applied across metal electrodes 26 fitted to respective sides of the composite film. The application of a voltage across the composite film results in deflection of the diaphragm as indicated in broken lines in FIG. 2. The use of multiple layers of PVDF film overcomes the problem that the typical amount by which an individual layer will reduce in thickness is less than a few hundred nanometres. Deflections of tens of microns can be achieved by the use of multiple layers.

Figure 3:
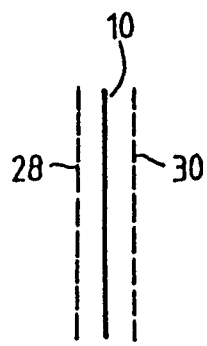

An electrostatically driven diaphragm may alternatively be employed, as shown diagrammatically by FIG. 3. The diaphragm 10 itself is a flexible metal or metallised, or otherwise conductively coated, plastics film disposed between two fixed perforated electrodes 28, 30 between which is applied the deflecting voltage from the deflecting means 20.

Figure 4:
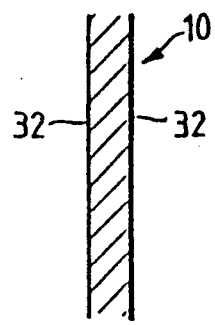

FIG. 4 shows an electro thermomechanical film (ETMF) as the diaphragm 10. The material has metal electrodes 32 applied on its surfaces and the application of a deflecting voltage between these electrodes causes the material to elongate and thin, in a similar manner to PVDF film.

Figure 5:
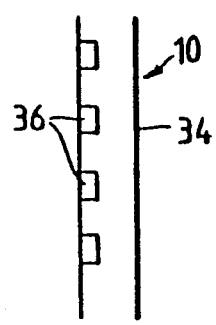

FIG. 5 shows an electromechanical arrangement for the diaphragm 10. A thin plastics film 34 is printed with a wiring "coil" and this cooperates electromagnetically with a plurality of magnets 36.

It will be appreciated that the sensing means and the deflecting means may both be regarded as similar transducers, one the inverse of the other. Hence, the sensing means 16 may be similar to any of the alternative deflecting means shown in FIGS. 2 to 5.

Figure 6:
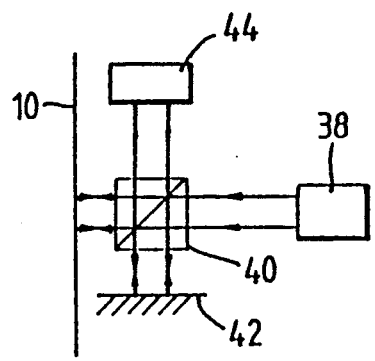
FIG. 6 shows an optical sensing means which may be used in the attenuating apparatus of FIG. 1; and, FIG. 7 is a diagram illustrating the servo operation of the attenuating means and showing how an external audio signal can be applied.

Another possible form of the sensing means is shown in FIG. 6. This arrangement uses a small Michaelson interferometer having a laser 38 which directs light to a beam splitter 40. One component of the light is directed on to the diaphragm 10 and the other component is directed on to a mirror 42, these two components being compared in a detector 44 the output of which is representative of the deflection of the diaphragm. The laser could be a helium neon laser or preferably a semiconductor laser. The detector 44 could be a silicon photodiode.

Figure 7:
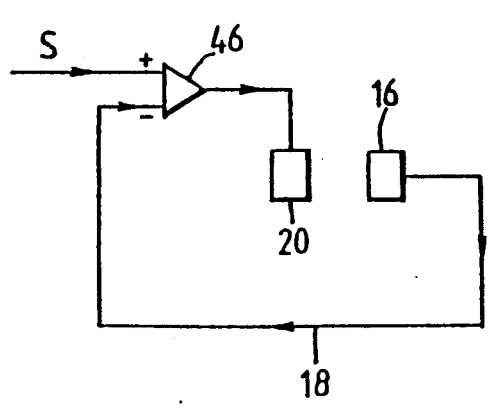

FIG. 7 shows the way in which the sensing means 16 drive the deflecting means 20 through a negative feedback loop. The feedback loop includes an operational amplifier 46 and the feedback loop operates such as to tend to reduce the output of the operational amplifier 46 to zero, in order to null the deflection of the diaphragm 10. It will be appreciated that if an external signal S is applied to the operational amplifier 46 as shown, this signal will be superimposed on to the system so that the diaphragm 10 will be deflected in accordance with the incoming signal S. Hence, if the signal S is an audio signal (for example a public address message or film soundtrack) this signal will be transmitted through the diaphragm 10 without attentuation and will reach the user's ears.

We claim:

1. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, the diaphragm being divided up into separate areas, each area having a corresponding sensing means cooperating with a deflecting means, so that each area of the diaphragm is separately driven.

2. Apparatus according to claim 1, which is incorporated in headphones.

3. Apparatus according to claim 2 wherein said sensing means is an optical sensor.

4. Apparatus according to claim 3 wherein said sensing means comprises an interferometer.

5. Apparatus according to claim 1, in which the diaphragm is incorporated in a component of an aircraft cabin.

6. Apparatus according to claim 1 wherein said sensing means is an optical sensor.

7. Apparatus according to claim 6 wherein said sensing means comprises an interferometer.

8. Apparatus according to claim 5 wherein said sensing means is an optical sensor.

9. Apparatus according to claim 8 wherein said sensing means comprises an interferometer.

10. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, wherein the deflecting means are driven from the sensing means through a negative feedback loop which acts to null the displacement of the diaphragm, and wherein said apparatus is incorporated in headphones.

11. Apparatus according to claim 10 wherein said sensing means is an optical sensor.

12. Apparatus according to claim 11 wherein said sensing means comprises an interferometer.

13. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, wherein the deflecting means are driven from the sensing means through a negative feedback loop which acts to null the displacement of the diaphragm, and wherein the diaphragm is divided up into separate areas, each area having a corresponding sensing means cooperating with a deflecting means, so that each area of the diaphragm is separately driven.

14. Apparatus according to claim 13 wherein said sensing means is an optical sensor.

15. Apparatus according to claim 14 wherein said sensing means comprises an interferometer.

16. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, said apparatus being incorporated in headphones.

17. Apparatus according to claim 16 wherein said sensing means is an optical sensor.

18. Apparatus according to claim 17 wherein said sensing means comprises an interferometer.

19. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, wherein the deflecting means are driven from the sensing means through a negative feedback loop which acts to null the displacement of the diaphragm, the feedback loop includes an amplifier with an input to which an audio signal can be fed whereby the diaphragm will be deflected in accordance with the audio signal, and wherein the diaphragm is divided up into separate areas, each area having a corresponding sensing means cooperating with a deflecting means, so that each area of the diaphragm is separately driven.

20. Apparatus according to claim 19 wherein said sensing means is an optical sensor.

21. Apparatus according to claim 20 wherein said sensing means comprises an interferometer.

22. Apparatus for attenuating noise, the apparatus comprising a diaphragm one side of which is subjected to the noise, sensing means for sensing the actual displacement of the diaphragm in response to the noise, and deflecting means responsive to the sensing means for deflecting the diaphragm in order to cancel the displacement, to attenuate noise transmitted from one side of the diaphragm to the other side of the diaphragm, wherein the deflecting means are driven from the sensing means through a negative feedback loop which acts to null the displacement of the diaphragm, the feedback loop includes an amplifier with an input to which an audio signal can be fed whereby the diaphragm will be deflected in accordance with the audio signal, and wherein said apparatus is incorporated in headphones.

23. Apparatus according to claim 22 wherein said sensing means is an optical sensor.

24. Apparatus according to claim 23 wherein said sensing means comprises an interferometer.

* * * * *